United States Patent [19]

Lin et al.

[11] Patent Number: 4,529,808
[45] Date of Patent: Jul. 16, 1985

[54] BI-SOLVENT SYSTEM FOR THE HYDROFORMYLATION OF ALLYL ALCOHOL USING A RHODIUM CATALYST

[75] Inventors: Jiang-Jen Lin, Round Rock; John F. Knifton, Austin, both of Tex.

[73] Assignee: Texaco Inc., White Plains, N.Y.

[21] Appl. No.: 576,513

[22] Filed: Feb. 2, 1984

[51] Int. Cl.$^3$ .......................................... C07D 307/20
[52] U.S. Cl. ..................................................... 549/475
[58] Field of Search ......................................... 549/475

[56] References Cited

U.S. PATENT DOCUMENTS 4,139,542 2/1979 Smith ................................... 549/475
4,356,125 10/1982 de Munck et al. .................. 549/475

Primary Examiner—Richard L. Raymond
Attorney, Agent, or Firm—Jack H. Park; David L. Mossman; Kenneth R. Priem

[57] ABSTRACT

A process is disclosed for preparing products such as 2-hydroxytetrahydrofuran which comprises contacting unsaturated compounds such as allyl alcohol with carbon monoxide and hydrogen in the presence of a rhodium carbonyl catalyst and a bi-solvent system. The bi-solvent system includes an aromatic solvent and an amide solvent and may be materials such as p-xylene and acetamide. Such a system provides for easy catalyst recovery since the rhodium catalyst is selectively soluble in the p-xylene whereas the desired product is conversely selectively soluble in the acetamide phase.

15 Claims, No Drawings

BI-SOLVENT SYSTEM FOR THE HYDROFORMYLATION OF ALLYL ALCOHOL USING A RHODIUM CATALYST

BACKGROUND OF THE INVENTION

1. Field of the Invention

This invention is related to the addition of hydrogen and carbon monoxide to olefin compounds to obtain hydroxy-substituted cyclic compounds in the presence of a rhodium-containing catalyst and is more particularly related to such an addition conducted in the presence of a bi-solvent system.

2. Description of Related Processes in the Field

The compound 2-hydroxytetrahydrofuran is an important intermediate for producing 1,4-butanediol. A number of methods have been discovered for hydroformylating various unsaturated compounds to useful products.

U.S. Pat. No. 4,209,467 assigned to Daicel, Ltd. teaches a low pressure hydroformylation process in which the catalyst is a reaction product of a cobalt carbonyl compound with a nitrogen-containing heterocyclic compound having an enolic hydroxyl group on the carbon atom adjacent to the ring-forming nitrogen atom, such as 2-hydroxypyridine. Ordinarily, the pressures employed therein are in the neighborhood of 10 to 100 atmospheres. Unsaturated compounds taught as suitable for this hydroformylation process include ethylenically unsaturated hydrocarbons such as ethylene, propylene, butadiene, etc. and compounds such as allyl alcohol, allyl acetate, etc.

Closer to the invention disclosed herein are methods which involve rhodium catalysts. U.S. Pat. No. 3,980,670 discloses a process for manufacturing methacrylic acid and butyrolactone by hydroformylation of allyl esters of lower carboxylic acids in the presence of rhodium carbonyl complex catalysts followed by oxidation of the resulting formyl compounds with molecular oxygen to produce 4-acetoxy-n-butyric acid and 3-acetoxy-isobutyric acid as the major products. See also German Offen. No. 2,106,243 to BASF. Unsaturated compounds such as propylene may be hydroformylated by means of rhodium/triphenylphosphine/carbonyl complexes formed in situ using a special pre-forming step described in U.S. Pat. No. 4,400,549.

Even more on point are the following patents. U.S. Pat. Nos. 4,064,145 and 4,083,882 describe a method for producing tetrahydrofuran and 1,4-butanediol by reacting synthesis gas with allyl alcohol under hydroformylation conditions in the presence of a rhodium carbonyl-phosphine catalyst complex and various inert solvents such as organic aromatics, aliphatic hydroxylic organic solvents, etc. In both patents, the allyl alcohol conversion was reported to be 99% and 4-hydroxybutanal was typically obtained in 87 wt. % yield. The major by-product was 2-methyl-3-hydroxypropanal (12 wt. %). A rhodium catalyst complexed with special bisphosphine monooxide ligands is taught as catalyzing the hydroformulation of olefinic compounds in the presence of dimethylformamide solvent according to U.S. Pat. No. 4,400,548. Again, two phase solvent systems are not disclosed.

In *J. Org. Chem.*, Vol. 45 (1980), 2132, C. U. Pittman, Jr. disclosed the hydroformylation of allyl alcohol to 4-hydroxybutanal and 3-hydroxy-2-methylpropanal using $HRh(CO)(PPh_3)_3$ and its polymer-bound analogues. The selectivity of normal/branched products was studied as the function of reaction parameters and ligands employed. The highest normal/branched selectivities were reported with 1,1'-bis(diphenylphosphino)-ferrocene at 80%. Benzene and o-xylene solvents were generally used.

In *J. of Mol. Cat.*, Vol. 11 (1981), 233-246, N. A. deMunck reported a heterogeneous gas phase hydroformylation of allyl alcohol using a supported $HRh(CO)(PPH_3)_3$ catalyst. A very high selectivity to 4-hydroxybutyraldehyde (97%) was achieved. However, the process is limited to only about 20% allyl alcohol conversion.

Kuraray disclosed the hydroformylation of allyl alcohol using rhodium catalyst in organic solvent such as benzene and toluene and a diphosphinoalkane. The overall n-/iso-ratio of the products were 86.6/13.4, (Kuraray, Japan. Pat. Open. No. 29412/1976, and No. 106407/1979 and *Chemical Economy of Engineering Review*, Vol. 12, No. 9, 1980). In additional patents (Kuraray, Japan. Pat. Open, No. 84508/1979 and British Pat. No. 1,493,154, 1977) to Kuraray, a modified Raney catalyst was claimed for the hydrogenation of hydroxybutyraldehydes into 1,4-butanediol and 3-methyl-1,3-butanediol.

Many of the systems described above lack good conversions of the unsaturated reactant compound and/or good selectivity to the desired product. Further, recovery of expensive rhodium catalysts is a problem in many of these processes. It would be an advance in the art if a method could be devised for hydroformulating compounds such as allyl alcohol while simultaneously solving the conversion, selectivity and catalyst recovery problems noted above.

SUMMARY OF THE INVENTION

The invention concerns a process for preparing 2-hydroxytetrahydrofuran which comprises hydroformylating allyl alcohol by reaction with carbon monoxide and hydrogen. A rhodium catalyst and a bi-solvent catalyst system are employed. One of the solvents is an aromatic compound and the other is an amide compound.

DESCRIPTION OF THE PREFERRED EMBODIMENTS

In general, the components of the hydroformylation reaction mixture, including the inert solvents, allylically unsaturated compound and rhodium catalyst may be added in any sequence as long as good agitation is employed to provide a good dispersion or a homogeneous reaction mixture. For example, the following represent some variations insofar as the addition of catalyst components, inert solvents and allyl alcohol addition that can be made without departing from the inventive process. These modifications include 1. The catalyst may be preformed and added to the reaction solvents prior to addition of the allyl alcohol and other inert solvent components.

2. Alternatively, to minimize stability problems with the catalyst, the catalyst is formed in situ, usually by mixing the inert solvents and allyl alcohol, followed by the addition of the catalyst components to form the reaction mixture.

3. After using either variation 1 or 2, the deoxygenated catalyst-containing reaction mixture is pressurized with CO and hydrogen and heated until the hydroxy tetrahydrofuran product is formed.

A rhodium catalyst is used in the present invention. Any rhodium-containing compound capable of forming a carbonyl under the reaction conditions can be used. This rhodium compound may be a carbonyl such as hexarhodium hexadecylcarbonyl. Preferably, the rhodium carbonyl is complexed with a phosphine ligand. Such catalysts are described in U.S. Pat. Nos. 4,064,145; 4,400,548 and 4,400,549, the pertinent portions of which are incorporated by reference herein. It is especially preferred that the catalyst be a rhodium carbonyl triphenylphosphine complex catalyst such as hydridocarbonyltris(triphenylphosphine)rhodium(I). This complex may be written as $HRh(CO)(PPh_3)_3$, where Ph represents a phenyl group. Preferably, an excess of the phosphine ligand is added to provide triphenylphosphine.

The method of this invention may be expected to be useful to hydroformylate many kinds of allylically-substituted unsaturated compounds. Suitable allylic compounds include allyl alcohol, alkyl-substituted allylic alcohols, alkyl allylic ethers such as methylallyl ether, ethylallyl ether and allyloctyl ether, as well as allylic esters such as allyl acetate, allyl propionate and allyl formate. It is preferred that the primary reactant is allyl alcohol. When allyl alcohol is employed, the desired product is 2-hydroxytetrahydrofuran.

As noted, a novel feature of the invention is the bi-solvent system. Both components of the bi-solvent must be inert with respect to the carbonylation reaction and both must be immiscible with respect to the other. Preferably, one solvent should be an organic, non-polar solvent such as an aromatic compound. Suitable aromatic compounds include benzene, toluene, ortho-xylene, meta-xylene, para-xylene, ethyl benzene and mixed xylenes, as well as mixtures thereof. Higher molecular weight aromatics with three or more alkyl substituents and more than one aromatic nucleus may also be useful in this application. p-Xylene is the preferred non-polar aromatic solvent component in which the rhodium catalyst is soluble.

The other solvent, to be immiscible, should be a polar compound. However, it should also be a solvent into which the desired product, 2-hydroxytetrahydrofuran, is easily soluble. In this way, the purpose of the two-phase solvent system is seen; namely, to separate the desired product from the catalyst to provide for easy recovery of the expensive rhodium catalyst. Suitable polar catalysts include various amides and alkyl amides, among others. These amides generally have the structure

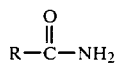

where R is hydrogen or a lower alkyl group of one to four carbon atoms. Preferably, the polar solvent is formamide or acetamide. Apparently, substituents on the nitrogen in compounds such as in the case of diethylformamide reduce the polar quality of the solvent enough to make it miscible with a non-polar solvent such as p-xylene as the examples will show. Thus, solvents such as diethylformamide would be unsuitable for this process. If the recommendations herein are followed, after the reaction, the mixture will separate cleanly into two phases which will permit easy recovery of the catalyst and the desired product.

The two solvent components of the bi-solvent system of this invention should be present during allyl alcohol carbonylation in weight ratios from 1:5 to 5:1 in order that the product mix cleanly separates into two phases—a rhodium catalyst-rich phase and a 2-hydroxytetrahydrofuranrich phase. Preferably, where the two solvent components are p-xylene and acetamide, the two solvents should be present in approximately equal amounts based upon weight.

The temperature range which can be employed for hydroformylation is a variable which is dependent upon experimental factors including the particular allylically unsaturated compound employed, the total pressure, the mole ratio of hydrogen and carbon monoxide used, the concentrations of reactants and catalyst, among other things. Using allyl alcohol as the substrate and rhodium carbonyltriphenylphosphine complex as a representative catalyst, an operable range is from about 25° C. to 125° C. or more when superatmospheric pressures of greater than 100 psig are employed. A narrower range of 50° C. to 120° C. represents the preferred temperature range when the aforementioned allyl alcohol is hydroformylated.

The pressure range which can be employed for hydroformylation is a variable which is also dependent on the factors mentioned above. Using rhodium carbonyltriphenylphosphine as a representative catalyst and allyl alcohol as the substrate, an operable pressure range is from about 100 to 5,000 psig or more, with a mole ratio of $H_2/CO$ being 1:1 when a temperature range of from about 25° C. to 125° C. is employed. A narrower range of from 500 to 1,500 psig represents the preferred pressure range when the narrower temperature range of 50° C. to 125° C. is employed.

The $H_2/CO$ mole ratio may be varied over a range of from 30:1 to 1:30 when suitable temperatures and pressures are employed. A preferred narrower range is from 2:1 to 1:2 of hydrogen/carbon monoxide.

Experimental variables are important in arriving at reaction times. Generally, substantial conversions (90% or higher) of the allyl alcohol to 2-hydroxytetrahydrofuran can almost always be accomplished within 18 hours, with 2 to 6 hours representing the more usual reaction time interval.

Experimental work indicates that an initial molar ratio of 10 moles to 10,000 moles of allyl alcohol per mole of rhodium-containing catalyst complex can be employed in most instances. The minimal ratio of 0.0001 moles of catalyst per mole of allyl alcohol is herein referred to as a "catalytic ratio" or "catalytic amount". Much higher ratios (i.e., 25 moles of substrate per mole of rhodium catalyst complex) are not harmful but are economically unattractive. For this reason the favored mole ratio ranges from 50 to 5,000 moles of allyl alcohol per mole of rhodium catalyst complex.

A suggested weight ratio of p-xylene solvent:amide solvent:allyl alcohol reactant is around 1:1:1. Using the process of this invention, at least 90 wt. % of the catalyst should be present in the resulting upper, non-polar p-xylene phase and at least 90 wt. % of the 2-hydroxytetrahydrofuran product should be present in the lower, polar amide solvent phase.

Allyl alcohol hydroformylation products, 2-hydroxytetrahydrofuran, may be isolated by the usual chemical or physical techniques, such as distillation, solvent extraction, chromatography, etc. Identification is by nuclear magnetic resonance and/or gas-liquid chromatography.

Conversion as defined herein represents the extent of conversion of the reacting allyl alcohol to other products. Conversion is expressed as a percentile and is calculated by dividing the amount of allyl alcohol consumed during hydroformylation by the amount of alcohol originally charged and multiplying the quotient by 100. The allyl alcohol conversion in the process of this invention can be at least 90%.

Yield, as defined herein, represents the efficiency in catalyzing the desired hydroformylation reaction relative to other undesired reactions. In this instance hydroformylation to 2-hydroxytetrahydrofuran is the desired lated by determining the amount of 2-hydroxytetrahydrofuran product formed, divided by the amount of allyl alcohol charged and multiplying the quotient obtained by 100.

Selectivity, as defined herein, is the efficiency in catalyzing a desired hydroformylation reaction relative to the other undesired conversion. Selectivity is expressed as a percentile and is calculated by determining the amount of 2-hydroxytetrahydrofuran product formed, divided by the total amount of $C_3$ plus $C_4$ products formed and multiplying the quotient obtained by 100. Selectivity can be at least 90% for the inventive process.

Having described the inventive process in general terms, the following examples are submitted to supply specific and illustrative embodiments.

EXAMPLE 1

To a 300 ml stainless steel stirred autoclave was charged hydridocarbonyltris(triphenylphosphine)rhodium(I) HRh(CO)(PPh$_3$)$_3$ (0.046 g), triphenylphosphine (1.3 g), allyl alcohol (7.0 g), p-xylene (7.0 g) and acetamide (7.0 g). The reactor was purged of air and pressured to 100 psi with a mixture of carbon monoxide and hydrogen (CO/H$_2$=1:1 molar ratio), then was heated to 60° C. The pressure was brought up to 800 psi and maintained during the process by the addition of CO/H$_2$ mixture (1:1 molar ratio) through a gas cylinder. After 4 hours, the reaction was stopped and the reactor was cooled to room temperature. The excess gas was vented from the reactor, following which a 23.0 g two-layer product solution was recovered.

The top layer (p-xylene rich), 5.0 g, contained 1050 ppm rhodium (ca. 95% of the Rh charged), but only about 4 wt. % concentration of 2-hydroxytetrahydrofuran. The bottom layer (product plus acetamide), 18.0 g, contained 14.5 ppm Rh (ca. 5% of Rh charged) and 7.7 g of 2-hydroxytetrahydrofuran.

Thus the Rh catalyst and 2-hydroxytetrahydrofuran were separated by two different liquid layers. The gas liquid chromatographic analysis of this product mix further showed:

| | |
|---|---|
| Allyl Alcohol Conversion, % | >90 |
| Selectivity to 2-Hydroxytetrahydrofuran, % | 95 |
| Estimated Yield of 2-Hydroxytetrahydrofuran, mole % | 74 |

Rhodium recovered in the product solution was essentially quantitative. 95% of the rhodium was in the top (p-xylene-rich) layer.

EXAMPLE 2

Following the procedures of Example 1, the 300 ml autoclave was charged with HRh(CO)(PPh$_3$)$_3$ (0.046 g), triphenylphosphine (1.3 g), allyl alcohol (7.0 g), p-xylene (7.0 g) and formamide (7.0 g). Reaction with carbon monoxide and hydrogen (CO/H$_2$, 1:1) was conducted at 60° C. and 800 psi for 4 hours. After cooling the reactor and depressurizing, a total of 22.7 g of two-phase liquid product was recovered. Analysis showed the top layer, rich in p-xylene, comprises 6.5 g and contained 620 ppm rhodium but only about 2% concentration of 2-hydroxytetrahydrofuran (0.2 g). The bottom layer (16.5 g) was found to contain 8.8 ppm rhodium and 7.4 g of 2-hydroxytetrahydrofuran. Gas-liquid chromatography analysis of the total product mix showed:

| | |
|---|---|
| Estimated Allyl Alcohol Conversion, % | 92 |
| Selectivity to 2-hydroxytetrahydrofuran, % | 95 |
| Estimated Yield of 2-hydroxytetrahydrofuran, mole % | 71 |

Rhodium recovery in the product solution was essentially quantitative.

EXAMPLE 3

Following the procedures of Example 1, the 300 ml autoclave was charged with HRh(CO)(PPh$_3$)$_3$ (0.046 g), triphenylphosphine (1.3 g), allyl alcohol (7.0 g), toluene (7.0 g) and acetamide (7.0 g). Reaction with carbon monoxide and hydrogen (CO/H$_2$, 1:1) was conducted at 60° C. and 800 psi for 4 hours. After cooling the reactor and depressurizing, a total of 22.7 g of two-phase liquid product was recovered. Analysis showed the top layer, rich in toluene, comprises 2.7 g and contained 1080 ppm rhodium but only about 7% concentration of 2-hydroxytetrahydrofuran (~0.2 g). The bottom layer (20.0 g) was found to contain 56.9 ppm rhodium and 7.4 g of 2-hydroxytetrahydrofuran. The proton-NMR analysis of the total product mix showed:

| | |
|---|---|
| Estimated Allyl Alcohol Conversion, % | >95 |
| Selectivity to 2-hydroxytetrahydrofuran, % | 84 |
| Estimated Yield of 2-hydroxytetrahydrofuran, mole % | 71 |

EXAMPLE 4

Following the procedures of Example 1, the 300 ml autoclave was charged with hexarhodium hexadecacarbonyl (0.0089 g), triphenylphosphine (1.3 g), allyl alcohol (7.0 g), p-xylene (7.0 g) and acetamide (7.0 g). Reaction with carbon monoxide and hydrogen (CO/H$_2$, 1:1) was conducted at 60° C. and 800 psi for 4 hours. After cooling and depressurizing the reactor, a total of 23.5 g of two-phase liquid product was recovered. Analysis showed the top layer, rich in p-xylene, comprised 4.5 g and contained 301 ppm rhodium but only a trace amount of unreacted allyl alcohol. The bottom layer (19.0 g) was found to contain 46.5 ppm rhodium, 2.4 g of 2-hydroxytetrahydrofuran and 4.6 g of unreacted allyl alcohol. The proton-nuclear magnetic resonance analysis of the total product mix showed:

| | |
|---|---|
| Estimated Allyl Alcohol Conversion, % | 34 |
| Selectivity to 2-hydroxytetrafuran, % | 73 |
| Estimated yield of 2-hydroxytetrahydrofuran, mole % | 23 |

EXAMPLE 5

The reaction mixture was HRh(CO)(PPh$_3$)$_3$ 0.042 g, Ph$_3$P (1.3 g), allyl alcohol (7.0 g , p-xylene (7.0 g) and diethylformamide (7.0 g). Similar reaction conditions to those of Example 1 were used. At the end of the reaction, gas-liquid chromatography analysis showed a 93% yield of 2-hydroxytetrahydrofuran was obtained. However, only a single-phase homogeneous product solution was observed.

EXAMPLE 6

The identical procedures were used as in Example 1 except that the following quantities were used: HRh(CO)(PPh₃)₃ (0.046 g), PH₃P (1.3 g), allyl alcohol (10 g), p-xylene (10 g) and acetamide (1.0 g). After four hour reaction, gas-liquid chromatography analysis showed a 96% yield of 2-hydroxytetrahydrofuran was obtained. The rhodium catalyst and the product were in a single homogeneous solution. This example demonstrates the need for the weight ratio of the aromatic hydrocarbon to the amide solvent to be in the range of 1:5 to 5:1.

Many modifications may be made by one skilled in the art without departing from the spirit and scope of the invention which are defined only by the appended claims. For example, solvents, proportions and reaction conditions could be changed to optimize the yield to 2-hydroxytetrahydrofuran.

We claim:

1. A process for preparing 2-hydroxytetrahydrofuran which comprises hydroformylating allyl alcohol by reaction with carbon monoxide and hydrogen in the presence of a rhodium carbonyl catalyst and a bi-solvent system comprising an aromatic hydrocarbon solvent and an amide solvent having the formula

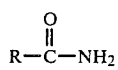

where R is hydrogen or a lower alkyl group of one to four carbon atoms and where the weight ratio of aromatic hydrocarbon solvent to amide solvent is in the range of 1:5 to 5:1, in a reaction mixture where after the reaction, the mixture separates into two immiscible liquid phases.

2. The process of claim 1 in which after the reaction the mixture separates into two liquid phases, an aromatic-rich phase and an amide-rich phase, where at least 90 wt. % of the rhodium catalyst is present in the aromatic phase and at least 90 wt. % of the 2-hydroxytetrahydrofuran product is present in the amide phase.

3. The process of claim 1 in which the reaction is conducted at a temperature in the range of from about 50 to 120° C. and at a pressure in the range from about 500 to 1,500 psi.

4. The process of claim 1 in which the catalyst is a rhodium carbonyl-triphenylphosphine complex together with excess triphenylphosphine.

5. The process of claim 1 in which the aromatic solvent is p-xylene.

6. The process of claim 1 in which the amide solvent is selected from the group consisting of formamide and acetamide.

7. The process of claim 1 in which the rhodium carbonyl catalyst is hydridocarbonyltris(triphenylphosphine) rhodium(I).

8. A process for preparing 2-hydroxytetrahydrofuran which comprises hydroformylating allyl alcohol by reaction with carbon monoxide and hydrogen in the presence of a rhodium carbonyl-triphenylphosphine complex catalyst and a bi-solvent system comprising p-xylene and an amide selected from the group consisting of formamide and acetamide, where the weight ratio of p-xylene to amide is in the range of 1:5 to 5:1, in a reaction mixture where after the reaction, the mixture separates into two immiscible liquid phases.

9. The process of claim 8 in which upon separation, at least 90 wt. % of the rhodium catalyst is present in the p-xylene rich phase and at least 90 wt. % of the 2-hydroxytetrahydrofuran product is present in the amide-rich phase.

10. The process of claim 8 in which the reaction is conducted at a temperature in the range of from about 50 to 120° C. and at a pressure in the range from about 500 to 1,500 psi.

11. The process of claim 8 in which the rhodium carbonyl-triphenylphosphine complex is hydridocarbonyltris(triphenylphosphine)rhodium (I).

12. The process of claim 8 in which the two solvents are present in approximately equal amounts based on weight.

13. A process for preparing 2-hydroxytetrahydrofuran which comprises hydroformylating allyl alcohol by reaction with carbon monoxide and hydrogen in the presence of a rhodium carbonyl-triphenylphosphine complex catalyst and a bi-solvent system comprisng p-xylene and an amide selected from the group consisting of formamide and acetamide, where the weight ratio of p-xylene to amide is about 1:1, in a reaction mixture where, after the reaction, the mixture separates into two liquid phases, a p-xylene phase and an amide phase where at least 90 wt. % of the rhodium catalyst is present in the p-xylene phase and at least 90 wt. % of the 2-hydroxytetrahydrofuran is present in the amide phase, allyl alcohol conversion being at least 90% and 2-hydroxytetrahydrofuran selectivity being at least 90%.

14. The process of claim 13 in which the reaction is conducted at a temperature in the range of from about 50° to 120° C. and at a pressure in the range of from about 500 to 1,500 psi.

15. The process of claim 13 in which the rhodium carbonyltriphenylphosphine complex is hydridocarbonyltris(triphenylphosphine)rhodium(I).

* * * * *